(12) United States Patent
Niemax et al.

(10) Patent No.: US 6,400,787 B2
(45) Date of Patent: Jun. 4, 2002

(54) TELEMETERING OF URANIUM OF PLUTONIUM IN GLASS

(75) Inventors: Kay Niemax, Schwerte; Lars Hiddemann, Bergkamen; Lothar Koch, Weingarten; Jean-Francois Babelot, Linkenheim-Hochstetten, all of (DE)

(73) Assignee: Euratom, Plateau Du Kirchberg (LU)

( * ) Notice: Subject to any disclaimer, the term of this patent is extended or adjusted under 35 U.S.C. 154(b) by 0 days.

(21) Appl. No.: 09/861,798

(22) Filed: May 21, 2001

Related U.S. Application Data (62) Division of application No. 09/029,730, filed as application No. PCT/EP96/03302 on Aug. 22, 1996, now Pat. No. 6,259,757.

(51) Int. Cl.[7] .............................................. G21C 17/00
(52) U.S. Cl. ..................... 376/257; 376/311; 376/317; 376/318; 250/336.1; 250/339.1; 250/339.07; 250/358.1; 250/492.1; 250/493.1
(58) Field of Search ................................. 376/257, 311, 376/317, 318; 250/358.1, 492.1, 339.07, 336.1, 339.1, 493.1

(56) References Cited

U.S. PATENT DOCUMENTS

| | | | | |
|---|---|---|---|---|
| 3,936,184 A | * | 2/1976 | Tanaka et al. ................. 355/15 |
| 4,024,407 A | * | 5/1977 | Meric et al. .................. 250/574 |
| 4,063,090 A | * | 12/1977 | Bernhardt .................... 250/284 |
| 4,645,342 A | * | 2/1987 | Tanimoto et al. ........... 356/318 |
| 4,714,628 A | * | 12/1987 | Eloy .......................... 427/53.1 |
| 5,133,901 A | * | 7/1992 | Peterson et al. ............. 252/626 |
| 5,627,641 A | * | 5/1997 | Mauchien et al. .......... 356/318 |
| 5,751,416 A | * | 5/1998 | Singh et al. ................. 356/311 |
| 6,034,768 A | * | 3/2000 | Fraser et al. ................ 356/316 |
| 6,137,073 A | * | 10/2000 | Brown ................... 204/157.21 |
| 6,259,757 B1 | * | 7/2001 | Niemax et al. ............. 376/257 |

FOREIGN PATENT DOCUMENTS

| | | | | |
|---|---|---|---|---|
| WO | WO 99/15865 | * | 9/1998 | ............. G01J/3/00 |

* cited by examiner

*Primary Examiner*—Michael J. Carone
*Assistant Examiner*—John Richardson
(74) *Attorney, Agent, or Firm*—Morgan & Finnegan, LLP (57) ABSTRACT

Described are a process and an apparatus for the remote measurement of uranium or plutonium in radioactive materials, in which the sample of the material to be analyzed is to be handled as little as possible. To attain that object it is proposed that the laser beam of a laser is focussed by means of a focussing unit onto the sample to be analyzed, so that a light-emitting plasma is generated, an image of the emission spectrum of the plasma is formed in a spectrograph by means of an imaging unit, and finally it is analyzed by means of an analyzing unit.

2 Claims, 10 Drawing Sheets

| Manufacturer | Laaber LWL GmbH, D-6090 Rüsselsheim |
|---|---|
| Fiber type | Individual fibers LWS 600 for $\lambda = 1064$ nm |
| Diameter | 600 $\mu$m |
| Length | 500 mm |
| Destruction threshold | 11-23 GW/cm$^2$ |
| | |
| Focussing optics: | |
| Manufacturer | LOT/ORIEL |
| Type | 77646, 2-lens system |
| Focal length $f_1$ | 35 mm |
| Focal length $f_2$ | 19 mm |
| Focal length $f_3$ | 19 mm |
| Lens material | Fused Silicia |
| Focus diameter | ca. 320 $\mu$m |

Fig. 3

| Manufacturer | Laaber LWL GmbH, D6090 Rüsselsheim |
|---|---|
| Fiber type | 4-armed light guide, fiber bundle LUV 105 with protective sheath MP for transmission from $\lambda = 200$nm |
| Diameter of the individual arms | 2 mm |

| Diameter at common end | 4 mm |
|---|---|
| Length of the arms | 700 mm |
| Total length | 1200 mm |
| Optics for coupling into the 4-armed LWL: | |
| Manufacturer | LOT/ORIEL |
| Type | 77646, 2-lens system |
| Focal length $f_1$ | 19 mm |
| Focal length $f_2$ | 35 mm |
| Lens material | Fused Silicia |
| Optics for imaging in the spectrograph: | |
| Manufacturer | Spindler & Hoyer |
| Type | Lens with focal length $f_1 = 170$ mm, matched to the spectrograph |
| Material | Suprasil |

| λ [nm] | spectral window [nm] | detector resolution [nm/pixel] |
|---|---|---|
| 200 | 7.04 | 0.0101 |
| 250 | 6.77 | 0.0097 |
| 288 | 6.53 | 0.0093 |
| 400 | 5.65 | 0.0081 |
| 425 | 5.36 | 0.0077 |
| 591 | 2.74 | 0.00393 |
| 600 | 2.70 | 0.0039 |

Legend:
- □ P-W 20μs
- ⊠ P-W 30μs
- ■ P-W 10μs

X-axis: Time shift [μs]
Y-axis: Signal/noise ratio

Fig. 19

|  | without light guide | with light guide |
|---|---|---|
| Diameter of the focal spot | ca. 90 μm | ca. 320 μm |
| Laser pulse energy | ca. 20 mJ | ca. 20 mJ |
| Radiation density | ca. $6.3*10^{10}$ W/cm$^2$ | ca. $5*10^{10}$ W/cm$^2$ |
| Signal/noise ratio (100 shots) U(I) 591.539 nm | ca. 153 | ca. 43 |
| relative detection limit (100 shots) U(I) 591.539 nm | ca. 270 ppm | ca. 950 ppm |
| amount of material removed (matrix: glass) | ca. 2 ng/shot | ca. 0.15 ng/shot |
| absolute detection limit (100 shots, matrix: glass) | ca. 54 pg | ca. 14 pg |

TELEMETERING OF URANIUM OF PLUTONIUM IN GLASS

This is divisional of co-pending application Ser. No. 09/029,730, filed Jul. 6, 1998, U.S. Pat. No. 6,259, 757.B1 which is a 371 of PCT/EP96/03302 Aug. 22, 1996.

The present invention concerns a process and an apparatus for the remote measurement of uranium or plutonium in radioactive materials, such for example in waste glasses.

Hitherto, for the purposes of determining radioactive elements in radioactive materials, a sample is mechanically taken from those materials and then investigated for the presence of such elements. In that procedure the persons dealing with the investigation operation handle and operate with the sample of the material to be analyzed, with those tasks being implemented in chambers which shield the radioactive radiation and in which there are arranged gripping tongs assemblies and the like which can be operated by the operator from outside the chamber. Processing the samples in the chambers is a highly complicated operation and is therefore correspondingly time-consuming.

Therefore the object of the present invention is to provide a process and an apparatus for the remote measurement of uranium or plutonium in radioactive materials, whereby the sample of the material to be analyzed has to be handled as little as possible.

The object of the invention is attained by means of a process for the remote measuring of uranium or plutonium in radioactive materials characterized by the process steps: generating a light-emitting plasma of a sample of the radioactive material by irradiating the sample with a laser beam, detecting the emission spectrum of the plasma, during which the plasma is flushed with an inert gas selected from the group consisting of dust-free air and argon, and analyzing the emission spectrum obtained. The process is carried out in an apparatus comprising a laser generating a laser beam focussed onto a sample of a radioactive material to produce a light-emitting plasma, forming an image of a spectrum of the light emitted by the plasma in a spectrograph and analyzing the spectrum recorded by the spectrograph.

In accordance with the invention it is proposed that a laser be provided, the laser beam of which can be focussed onto the sample to be analyzed of the radioactive material. When the laser beam strikes the sample a tiny amount thereof is ablated, and for that reason this is called a quasi-non-destructive process. In this operation the laser produces a plasma of the sample, from which light is emitted. An image of the emission spectrum of the plasma is formed in a spectrograph and then evaluated by means of an analyzing unit. The spectral lines discovered then permit suitable information to be obtained about the presence of uranium or plutonium in the sample.

It is particularly advantageous if there is provided a delay unit which delays the beginning of the analyzing process, that is to say in particular mathematical integration of the measured emission spectra in respect of time, in regard to the laser pulse emission time. In that way it is possible to set an optimum signal/noise ratio of given spectral lines relative to each other, by varying that delay time. It is further possible to guarantee that analysis is only effected when the material removed from the sample is completely atomized.

The focussing unit for focussing the laser beam can be arranged directly at the laser so that a laser beam leaving the focussing unit of the laser can strike the sample directly through free space. It is further possible for the imaging unit which forms in the spectrograph the image of the light emitted by the laser-generated plasma to be arranged directly at the spectrograph itself. In this case also the emitted light passes directly through free space to the spectrograph. By virtue of the relatively large distances that the laser light and the light emitted by the sample plasma have to cover in free space, corresponding dispersion effects and losses in intensity of the laser beams can occur.

Preferably therefore on the one hand the laser beam is moved closer to the sample and on the other hand the light emitted by the sample is guided earlier in spatial terms so that the distances to be covered overall by the light beams in free space are reduced.

In such an embodiment of the invention there is provided a measuring head which can be fitted onto the sample. The feed of the laser beam to the measuring head and transmission of the light emitted by the sample from the measuring head to the spectrograph is effected in each case by means of light guides. The measuring head has a plurality of tubular connecting portions in which the lens systems of the focussing unit and the imaging unit respectively are arranged. In that assembly the optical axes of the lens systems are so oriented that the extensions thereof extend substantially through that region in space in which the laser-generated plasma of the sample occurs during the measurement procedure.

At least one feed conduit can be provided at the underside of the measuring head, through which feed conduit a flushing or scavenging fluid for shielding the plasma from the ambient air is fed to a chamber which is provided in the measuring head and in which the sample is disposed. The flushing or scavenging fluid may be an inert gas, preferably argon, or dust-free air.

To adjust optimum coupling of the laser beam into the light guide leading to the measuring head, there is provided an light guide coupling-in unit which is fixedly connected to the housing of the laser and which makes it possible for the light guide end that is towards the laser on the one hand to be rotated about its two transverse axes and on the other hand to be linearly displaced in the direction of said transverse axes and its longitudinal axis.

An embodiment of the invention is described by way of example hereinafter with reference to the accompanying drawings in which.

Figure 1:
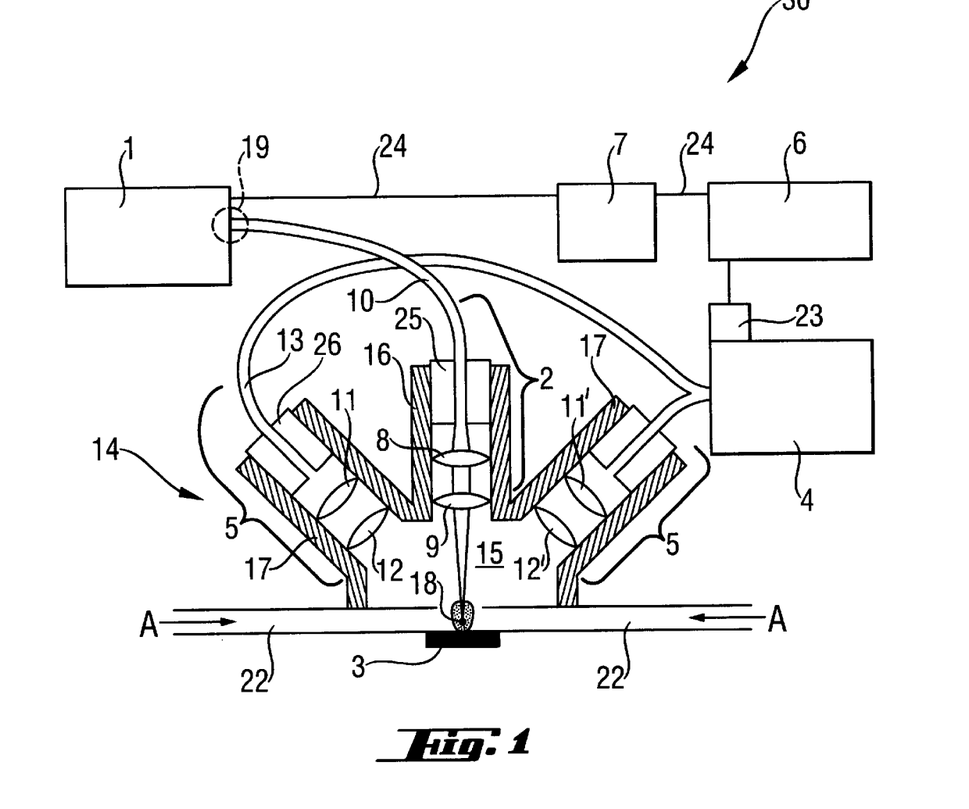
FIG. 1 is a side view of an embodiment of the apparatus according to the invention.

The apparatus 30 according to the invention as illustrated in FIG. 1 has an Nd:YAG laser (Spectron SL 401), a spectrograph 4 with detector unit 23, an analyzing unit 6 and a delay unit 7 arranged between the analyzing unit 6 and the laser 1. A computer (not shown) is connected to the detector unit 23. The analyzing unit 6 is the four-channel analyzer system OMAIII from EG&G. The delay unit 7 is connected to the laser 1 and the analyzing unit 6 by way of suitable signal lines 24.

To produce vaporization of the sample 3 the laser 1 is operated with its fundamental wavelength of 1064 nm and a pulse length of 5 ns. The pulse energy is preferably 20 mJ.

Figure 2:
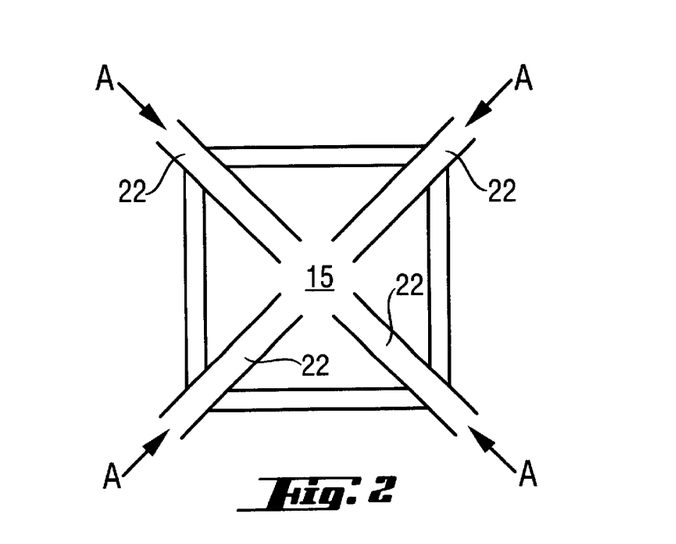
FIG. 2 is a view from below of the apparatus according to the invention as shown in FIG. 1.

The measuring head 14 which as shown in FIG. 2 is of a square configuration in plan can be fitted to the sample 3. Arranged thereon are a total of five tubular connecting portions 16, 17, of which only three can be seen in the side view in FIG. 1.

The focussing unit 2 comprising the light guide 10 and the lenses 8 and 9 is arranged in the perpendicularly upwardly projecting portion 16 of the measuring head 14, in which respect it will be appreciated that the light guide 10 extends only over a comparatively short length within the connecting portion 16. The other four connecting portions 17 which project laterally away from the measuring head accommodate the four imaging units 5 each comprising the light guide 13 and the lenses 11, 12 and 11', 12' respectively. Because of the four imaging units 5 provided here, reference is also made to a four-armed light guide 13. The two connecting portions 17 which cannot be seen in FIG. 1 are disposed one behind the other in the direction of viewing onto FIG. 1 and symmetrically with respect to the plane of the drawing in FIG. 1. That arrangement ensures that an image of the maximum possible part of the light which is emitted in all directions in space is formed in the spectrograph 4.

Figure 3:
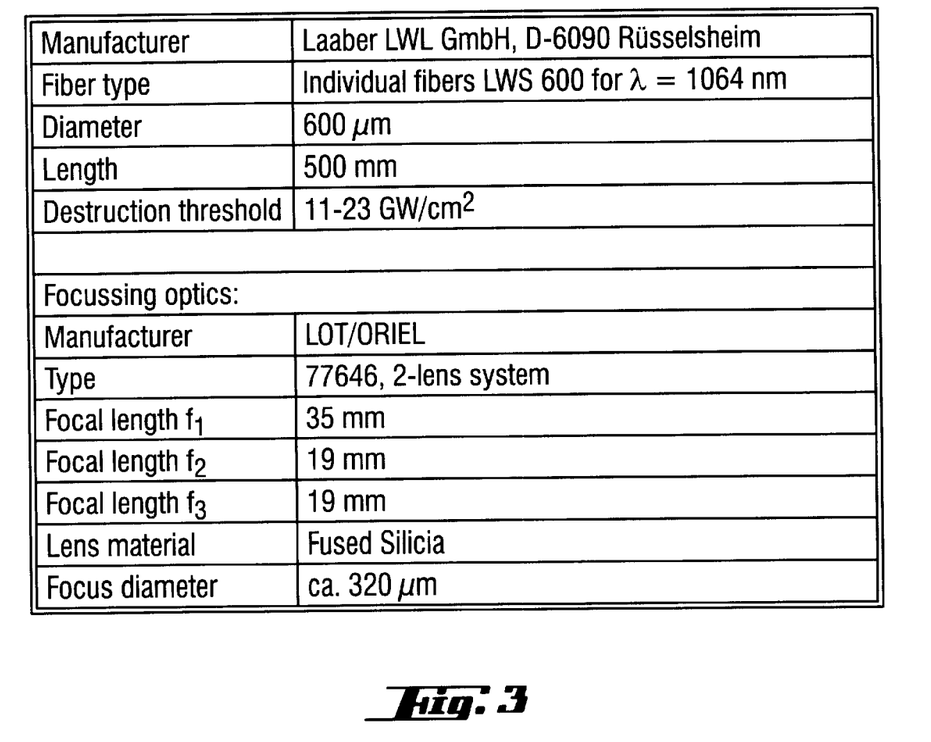
FIG. 3 shows a table with data of the fiber optics used for transportation of the Nd:YAG laser beam and the focussing optics.
Figure 4:
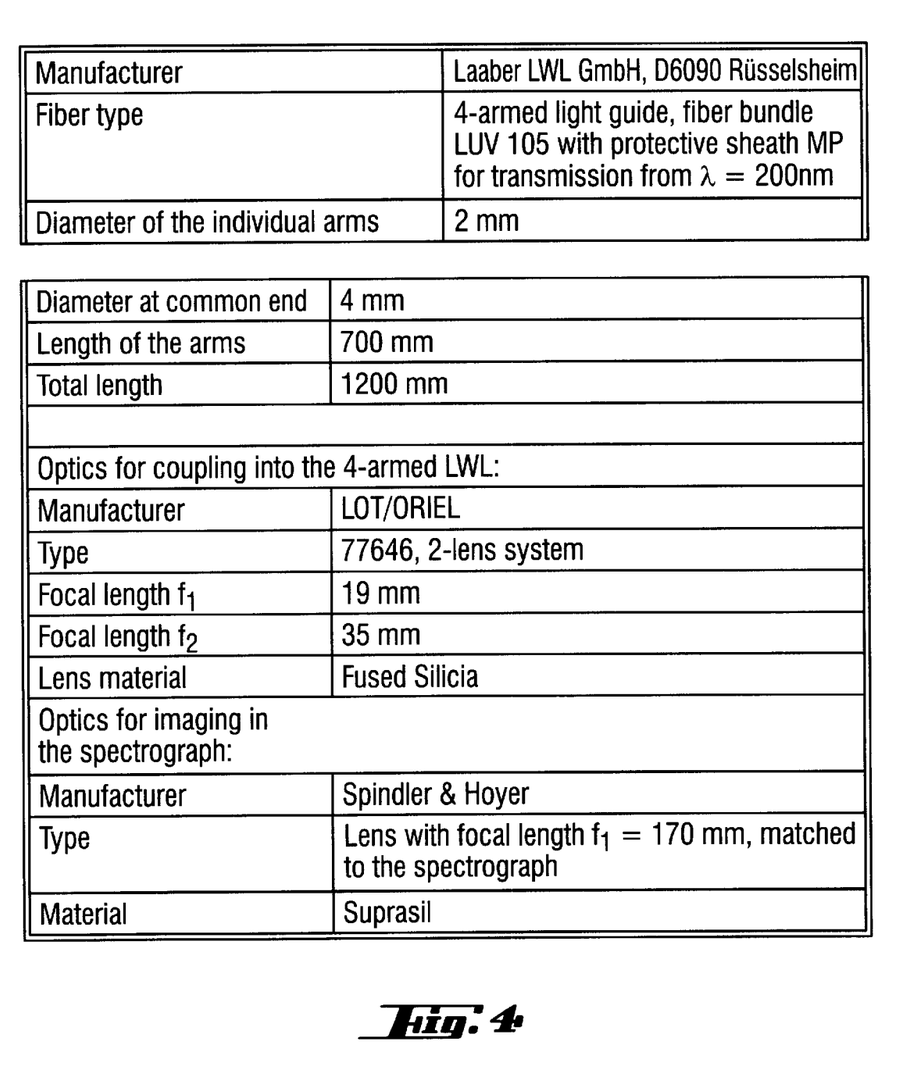
FIG. 4 shows a table with data of the fiber optics used for forming the image of the plasma.

The light guides 10 and 13 are held in the connecting portions 16 and 17 by guide portions 25 and 26 respectively. The light guides used are preferably glass fibers or glass fiber cables. The technical data of the focussing and fiber optics of the focussing unit 2 can be seen in the table illustrated in FIG. 3. The technical data of the focussing and fiber optics of the four imaging units 5 are contained in the table shown in FIG. 4.

As can best be seen from FIG. 2 the measuring head 14 has at its underside four feed conduits 22 through which a flushing or scavenging fluid flow can be fed as indicated by the arrows A into the chamber 15 of the measuring head 14. In that situation the flushing or scavenging fluid flow is intended to flow along the surface of the sample 3 and is intended to be of such a vertical extent that it flows as completely as possible around the laser-generated plasma 18. The fact that a flushing or scavenging fluid flows around the plasma means that disturbances to the plasma such as for example a reduction in plasma temperature due to air are avoided. The use of the inert gas argon as the flushing or scavenging fluid has proven to be particularly desirable. Preferably an argon flow of about 40 l/h is selected.

Figure 5:
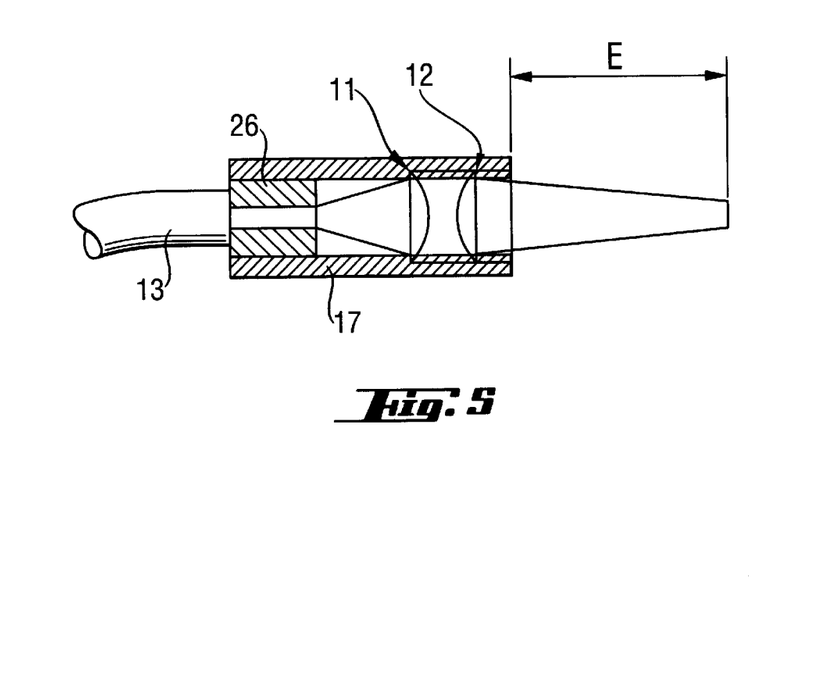
FIG. 5 shows the optics for coupling the light emitted by the laser-generated plasma into the four-armed light guide.

FIG. 5 shows the structure of the optical systems used for coupling into the four-armed light guide 13. It is possible in particular to see the working spacing E of the 2-lens systems 11, 12 of the imaging units 5 in which the light-emitting plasma 18 must occur. The imaging units 5 used make it possible also to form the image of and analyze radiation from layers of the plasma 18, which are near to the surface.

Figure 6:
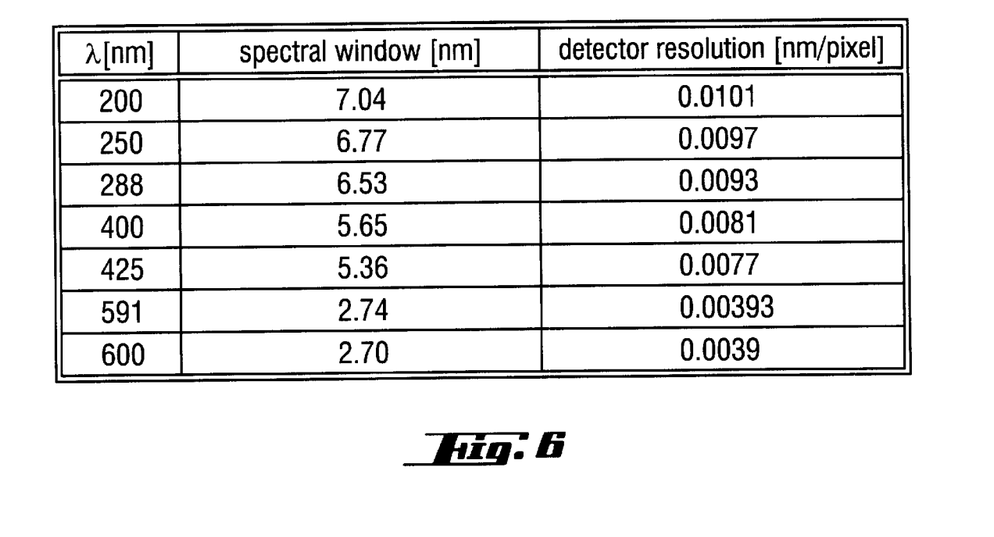
FIG. 6 shows a table with data relating to the spectral window and detector resolution in different wavelength ranges.

The table of FIG. 6 shows the pixel width and the simultaneously observable spectral window in various spectral regions of the four-channel analyzer system used.

Figure 7:
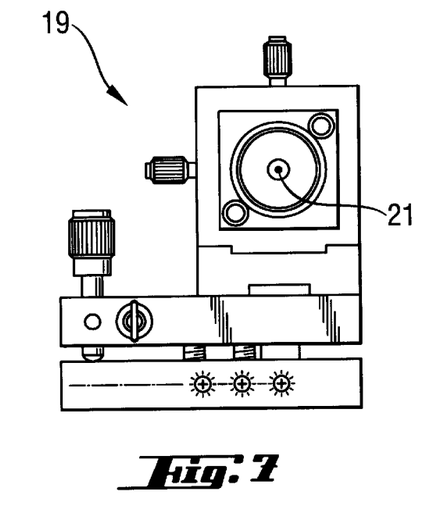
FIG. 7 is a front view of an light guide coupling-in unit according to the invention of Newport MF 91-CL type.
Figure 8:
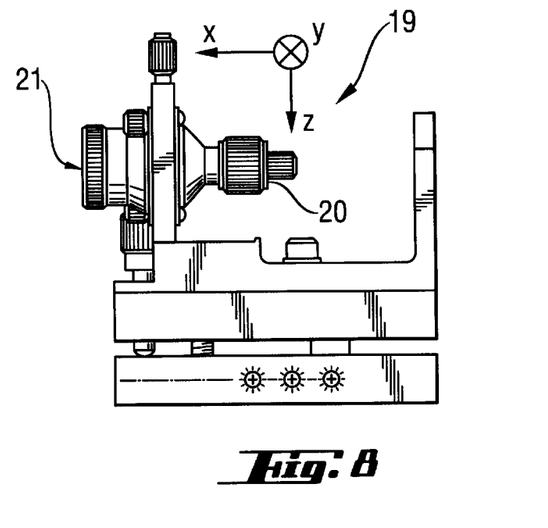
FIG. 8 is a side view of the light guide coupling-in unit according to the invention as shown in FIG. 7.
Figure 9:
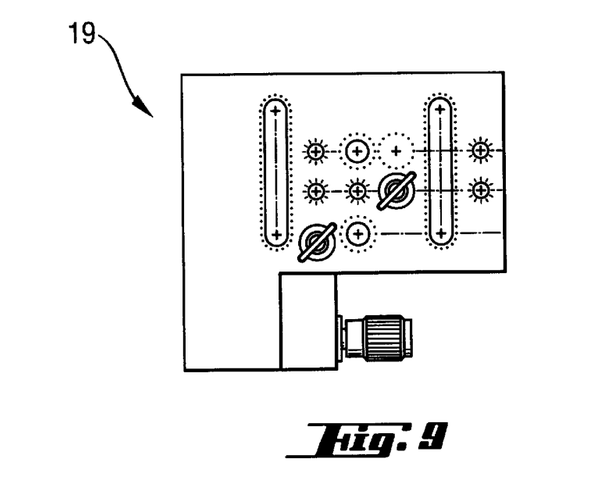
FIG. 9 is a view from below of the light guide coupling-in unit according to the invention as shown in FIG. 8.

FIGS. 7, 8 and 9 show the light guide coupling-in unit 19. It serves for optimum coupling of the laser beam coming from the laser 1, into the light guide 10. It has a laser beam introduction opening 21 and a light guide connection 20. The entire light guide coupling-in unit 19 is mechanically releasably fixed to the housing of the laser 1 so as to avoid disadjustment of the light guide fibers relative to the laser beam and thus possible destruction of the light guide fiber end surfaces in the event of disadjustment. To provide protection from impurities of the light guide fiber end surfaces, the fiber ends are flushed with dust-free air. A quartz lens with a focal length of 55.8 mm at the laser wavelength of 1064 nm is used for coupling the laser beam into the light guide fiber. The light guide fiber with a core diameter of 600 $\mu$m is positioned about 14 mm behind the focal point of the lens.

For optimum adjustment of the light guide fiber end relative to the laser beam, the light guide is allowed a total of five degrees of freedom. As shown in FIG. 8, at its end towards the laser 1, the light guide 10 which is connected to the light guide connection 20 is pivotable about its two transverse axes y and z and is linearly displaceable in the direction of those two transverse axes and its longitudinal axis x.

To prevent the fiber end surface being destroyed by excessively high levels of intensity, during the adjustment operation an attenuation filter is disposed between the laser 1 and the fiber of the light guide 10 so that, with a pulse energy of about 10 mJ, only about 0.01 mJ/pulse is coupled into the light guide fiber.

Figure 10:
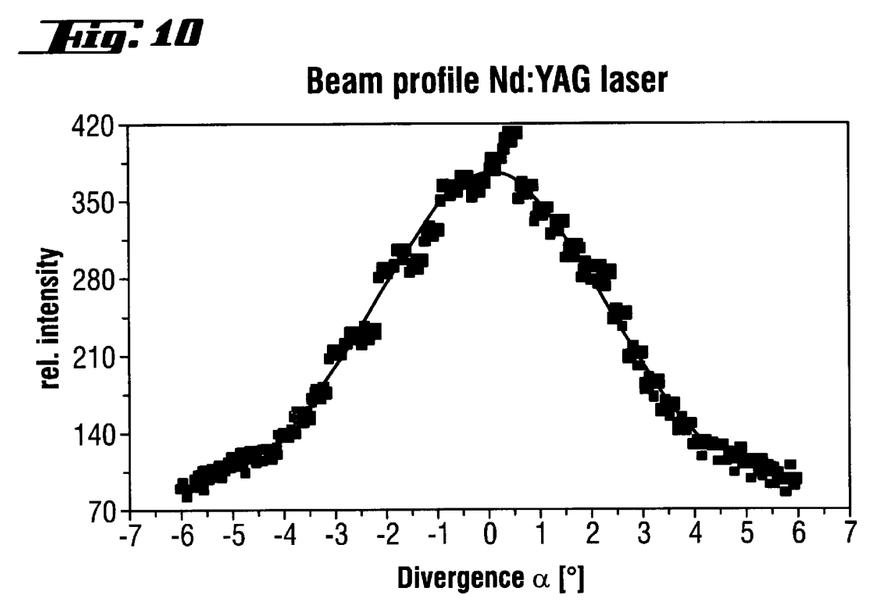
FIG. 10 is a beam profile of the Nd:YAG laser beam downstream of the light guide.

FIG. 10 shows the result of an investigation of the beam profile of the light issuing from the fiber of the light guide 10, which was obtained by means of a photodiode cell. This is the beam profile of the laser beam downstream of the light guide fiber with optimum coupling-in. It can be seen that the profile is symmetrical. After careful adjustment of the light guide fiber pulse energies of up to 30 mJ are coupled into the fiber without any problem. Those pulse energies are still about an order of magnitude beneath the specified destruction threshold of the light guide 10.

Figure 11:
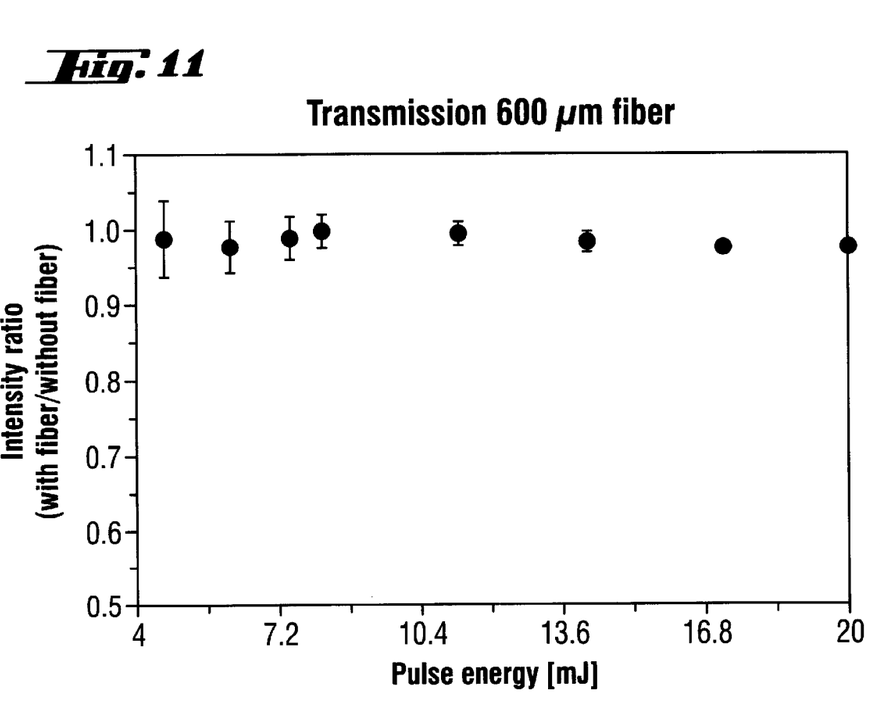
FIG. 11 shows the transmission of the light guide in dependence on the coupled-in pulse energy.

As shown in FIG. 11, it was not possible to detect any transmission losses within the limits of measuring accuracy, in the light guide 10. The measurement procedures involved operating with a pulse energy of 20 mJ, while the radiation density (about 0.8 GW/cm$^2$) of the light guide fiber end surfaces was about an order of magnitude below the destruction threshold.

The measurements with the embodiment described herein, that is to say with the light guides 10 and 13 and the measuring head 14, were compared with measurements which were implemented with another embodiment according to the invention which does not have a measuring head 14 and light guides 10 and 13, but in which the laser beam could strike the sample 3 directly from the laser 1 through free space and the light emitted by the plasma 18 could pass directly through free space into the spectrograph 4. The measurements associated with those two embodiments are referred to hereinafter as "measurements with light guide" and "measurements without light guide".

In the case of the measurements with light guide, a focus radius of about 320 $\mu$m was produced on the sample 3. In the measurements without light guide a maximum signal/noise ratio was found to occur with a laser energy of 20 mJ and a focus radius on the sample 3 of 90 $\mu$m, which corresponds to a radiation strength of about $6.3 \times 10^{10}$ W/cm$^2$. In the measurements with light guide the radiation density at the same pulse energy of the laser 1 was only about $5 \times 10^9$ W/cm$^2$, because of the larger focus diameter. That resulted in a sample removal which was about an order of magnitude less.

Figure 12:
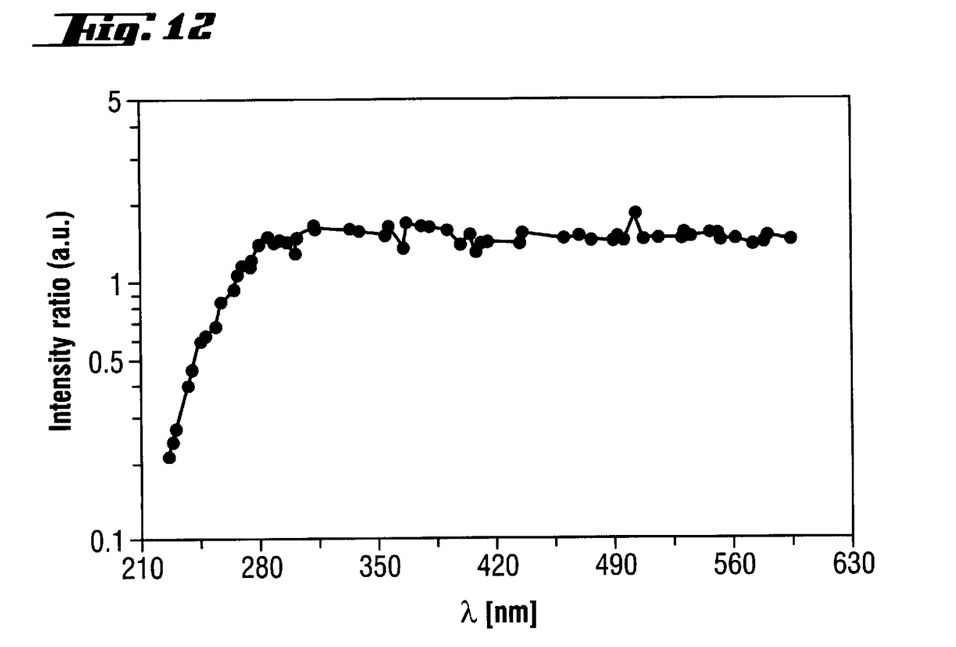
FIG. 12 shows the relative transmission of the four-armed light guide.

FIG. 12 shows the relative transmission of the four-armed light guide 13 for plasma radiation in the wavelength range between 200 and 600 $\mu$m. Transmission measurement was effected by means of a mercury vapor lamp. The transmission curve shows the relative configuration with all optical components in the event of measurements in air. The intensity ratio of measurements with and without light guide is plotted in relation to wavelength. It can be clearly seen that there is a falling transmission configuration below a wavelength of about $\lambda=280$ nm.

Figure 13:
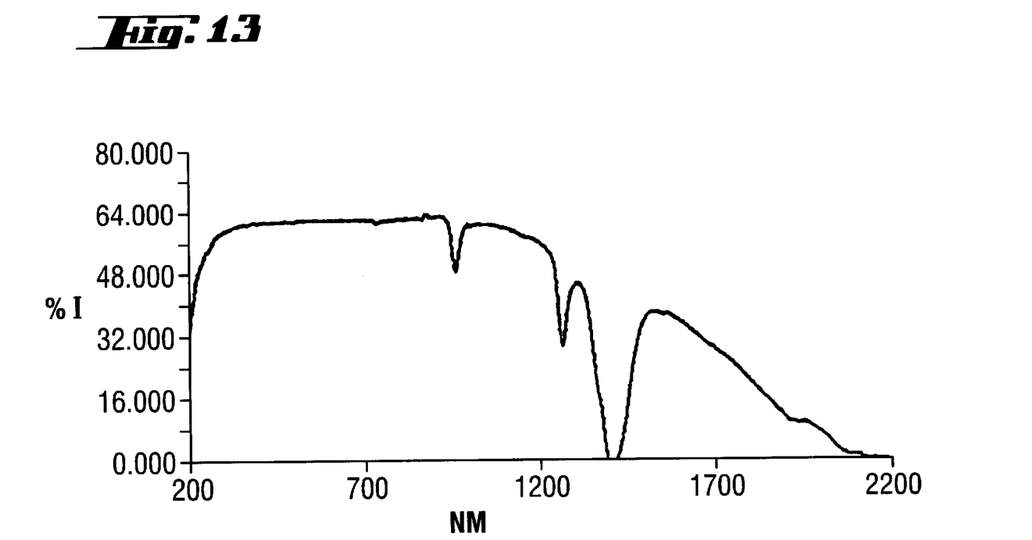
FIG. 13 shows the absolute transmission, as specified by the manufacturer, of the four-armed light guide.

FIG. 13 shows the absolute transmission, as specified by the manufacturer, of the light guide 13. The maximum absolute transmission is about 64%.

Figure 14:
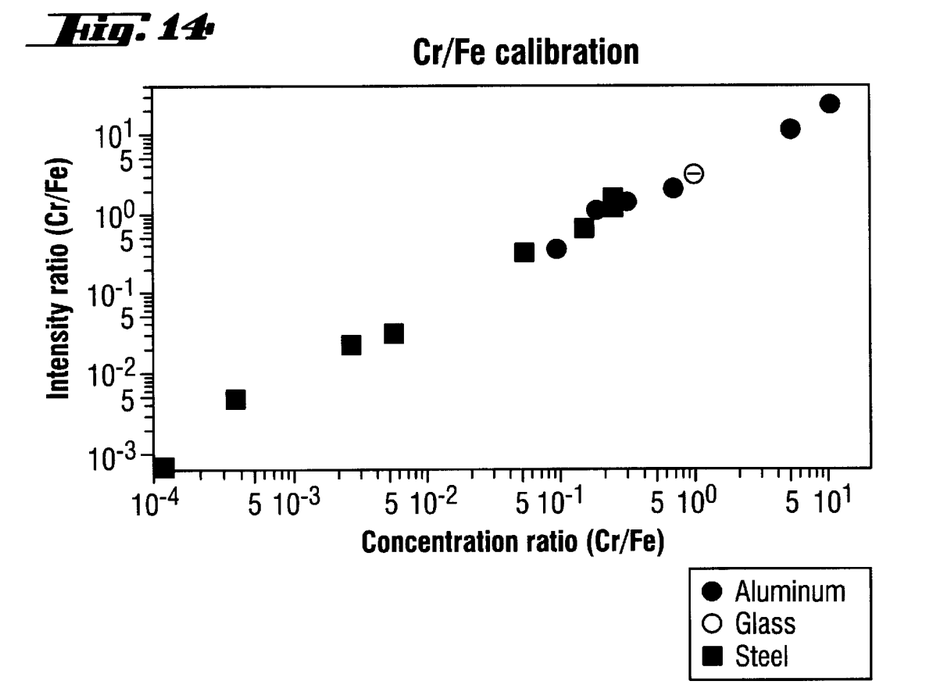
FIG. 14 shows a chromium/iron calibration measurement with three different matrices.

FIG. 14 shows a calibration measurement in respect of chromium as against iron with three different matrices (steel: NBS-sample, glass: sample from Hoesch, aluminum: samples from Pechiney and Alusuisse). Atom emission lines at 425.435 nm (Cr(I)) and 302.639 nm (Fe(I)) were used. The intensity ratio is plotted in relation to the concentration ratio. Measurement was also effected with a time delay of 6 $\mu$s after the laser pulse (pulse energy 20 mJ). The integration time was 40 $\mu$s. 50 spectra were added up. The gradient of the evening-out straight line is one in a double-logarithmic representation. All measurement data lie on the straight line, within 5%. This shows that matrix-independent measurement is possible. This information is important for determining uranium and plutonium in glasses of different compositions. Slight changes in the composition of the fused-in sample material can alter absorption and reflection of the laser radiation, the amount removed and the plasma parameters. If however lines with similar excitation energy are selected, then upon complete atomization of the material removed and upon the assumption of a thermodynamic equilibrium the intensity ratio is proportional to the concentration ratio and thus substantially independent of the sample composition and the plasma temperatures. Samples 3 in respect of which different amounts are removed and in respect of which different temperatures occur in the laser-generated plasma 18 can thus be compared together.

Figure 15:
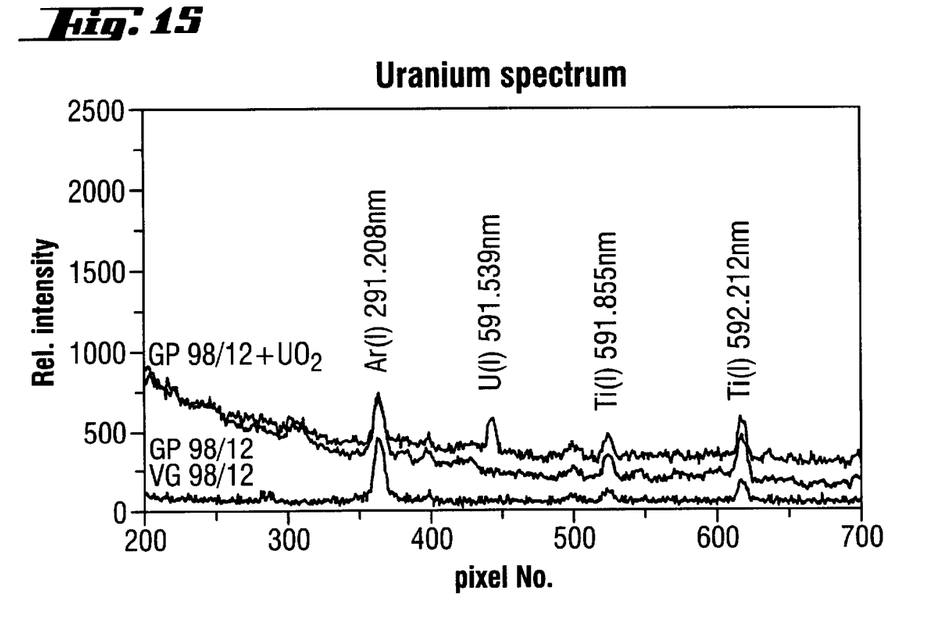
FIG. 15 shows the emission spectra of the glass samples VG 98/12, GP 98/12 and GP 98/12+U02 at 590 nm.

FIG. 15 shows spectra of the glass samples VG 98/12, GP 98/12 and GP 98/12+0.98% U02. 50 spectra were integrated in each case, with a delay of 6 $\mu$;s and an integration time of 20 $\mu$s. The sample removal was about 0.15 ng/shot with a radiation density of $5 \times 10^9$ W/cm$^2$. Besides the uranium atom emission line at 591.539 nm, it can be seen that there are also two emission lines of the matrix constituent titanium (Ti(I) 591.855 nm and Ti(I) 592.212 nm). and an atom lines in respect of the protective gas argon (591.208 nm).

Figure 16:
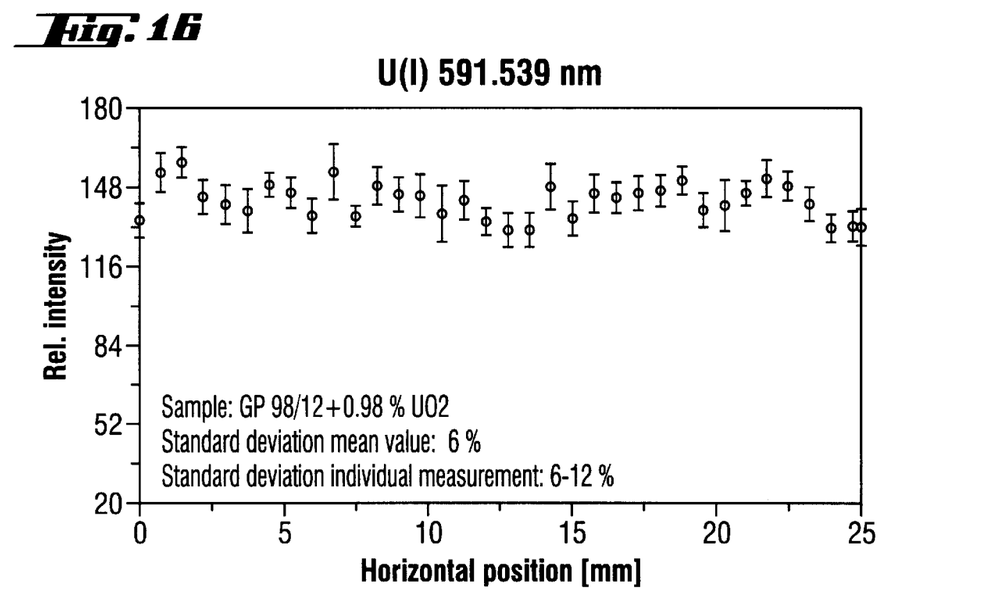
FIG. 16 shows a measurement in relation to uranium distribution in the glass sample GP 98/12+U02.

The measurement operation shown in FIG. 16 was implemented under the same measuring conditions in relation to homogeneity of the distribution of uranium in the sample GP 98/12+U02: Each measurement point represents the mean value from five measurements. It exhibits relatively homogenous uranium distribution, relative to the diameter of the focal spot of 320 $\mu$m. The standard deviation of the individual measurements is between 6 and 12% while that of the mean value is 6%.

Figure 17:
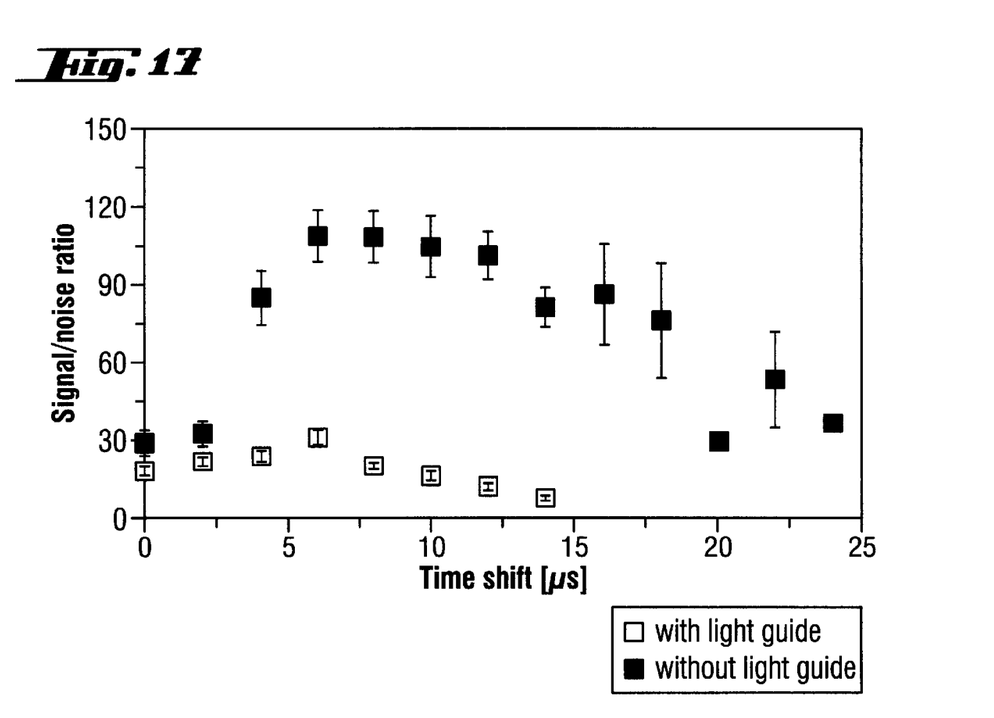
FIG. 17 shows the time dependency of the signal/noise ratio of the uranium atom line 591.539 nm, measured with and without light guide with an integration time of 20 $\mu$s.

FIG. 17 shows the signal/noise ratio of the uranium atom line 591.539 nm in dependence on time. Both in measurement with a light guide and also in measurement without a light guide, a maximum ratio can be seen at a time shift of 6 $\mu$s. Admittedly, the intensity of the analysis lines is higher with shorter delay times, but they are on a very high foundation (recombination continuum of the plasma). In addition there is a certain matrix dependency with short time delays because the material removed is not yet completely atomized.

The level of noise can be reduced by cooling the detector 23. That gives an improvement in the signal/noise ratio and thus also the detection limit.

When using higher laser pulse energies, greater levels of line intensity are to be expected, due to the greater degree of removal. However the time window then has to be re-established for an optimum signal/noise ratio.

Because of the lower level of intensity in the laser focus, the degree of sample removal in the case of measurements with a light guide is less than in the case of measurements without a light guide. However the measured intensity of the analysis lines is about 66% greater than in the case of measurements without a light guide if the degree of sample removal is comparable. due to a reduction in laser intensity, in the measurements without a light guide.

Figure 18:
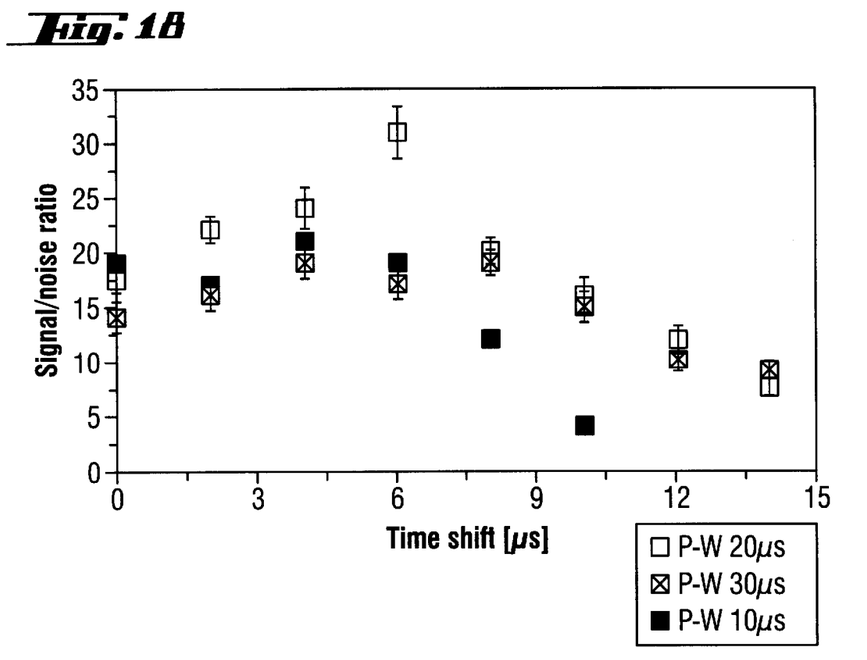
FIG. 18 shows the time dependency of the signal/noise ratio at three different integration times, namely 10 $\mu$s, 20 $\mu$s and 30 $\mu$s, measured with the measuring head.

FIG. 18 shows the time dependency of the signal/noise ratio with different integration times (10 $\mu$s, 20 $\mu$s and 30 $\mu$s). An optimum ratio is obtained with an integration time of 20 $\mu$s and a delay of 6 $\mu$s.

Figure 19:
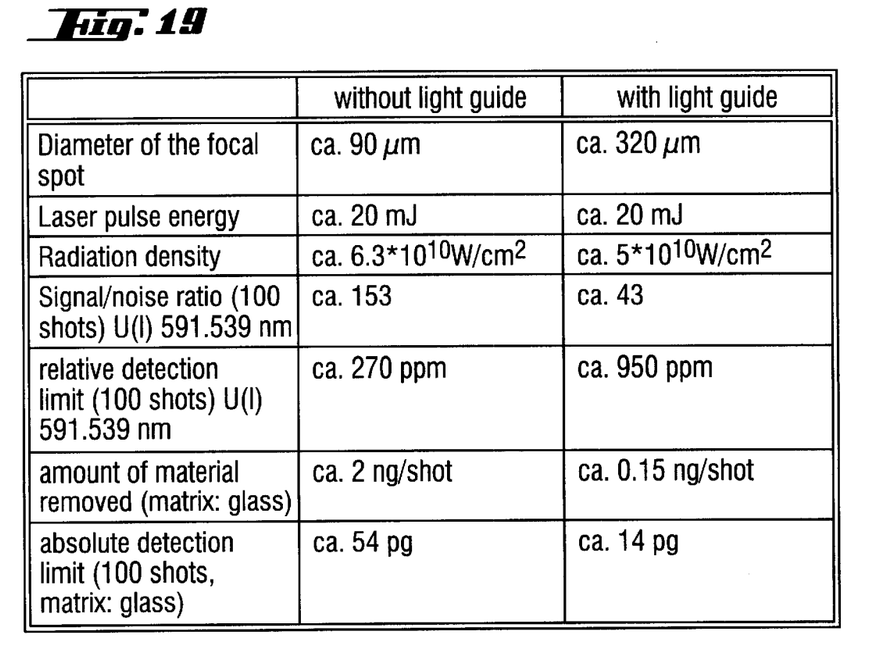
FIG. 19 shows a comparison of the results of the measurements according to the invention with and without light guide.

The table illustrated in FIG. 19 compares the measurements according to the invention without light guide 10, 13 on the one hand and with a light guide 10, 13 on the other hand. The comparison of the results shows that the absolute detection limits for uranium are lower in the case of measurements with a light guide than in the case of measurements without a light guide. The detection limit could be reduced approximately by the factor of 2 –3 if the detector 23 were to be cooled, in which case flushing of the detector 23 with a dry gas would of course be required. In addition higher levels of pulse energy result in a greater degree of removal and, with a suitable choice in regard to delay of detection, lower relative detection limits. It would also be advantageous to use a spectrograph 4 of the highest possible resolution so that stronger detection lines which previously could not be adopted by virtue of line interference phenomena can be utilised for determining concentration.

The apparatus according to the invention permits rapid analysis, of a simple structure, of highly radioactive samples 3. The apparatus required for analysis of the light emitted is transportable, in which respect during the measurement operation the measuring head 14 and the light guides 10, 13 represent stationary units while the laser 1, the spectrograph 4 and the detector 23 with connected computer can be installed in a mobile unit. The advantage of the measuring head 14 is in particular that it can be positioned as desired, while in addition it is possible to use flexible bendable light guides 10, 13 of very great length. Furthermore the measurements take place under an argon flow at atmospheric pressure so that there is no need to use closed sample chambers with expensive mechanisms for sample interchange. The measuring head 14 can be positioned at the sample 3 by means of a manipulator or a robot arm so that the experiment can be conducted under remote control and without direct contact with radioactive material.

What is claimed is:

1. A process for the remote measurement of uranium or plutonium in radioactive materials characterized by the following steps:

generating a light-emitting plasma of a sample to be analyzed by means of a laser beam, forming an emission spectrum of the plasma in a spectrograph, flushing the plasma with dust-free air for the purpose of shielding the plasma from disturbance effects due to the ambient air during the forming of the emission spectrum, and analyzing the emission spectrum.

2. A process as set forth in claim 1, characterized in that the beginning of the analysis operation is delayed relative to the laser pulse emission time.

* * * * *